United States Patent [19]
Bossert et al.

[11] 3,946,027
[45] Mar. 23, 1976

[54] 3,5,6-TRICARBOXY-4-PYRIDYL-1,4-DIHYDROPYRIDINE DERIVATIVES

[75] Inventors: Friedrich Bossert; Horst Meyer, both of Wuppertal; Wulf Vater, Opladen, all of Germany

[73] Assignee: Bayer Aktiengesellschaft, Germany

[22] Filed: Nov. 15, 1974

[21] Appl. No.: 523,967

Related U.S. Application Data
[62] Division of Ser. No. 399,850, Sept. 24, 1973, Pat. No. 3,905,983.

[30] Foreign Application Priority Data
Sept. 30, 1972 Germany............................ 2248150

[52] U.S. Cl. 260/295.5 R; 260/256.4 C; 260/287 R; 260/294.8 F; 260/294.8 G; 260/294.9; 260/295 R; 260/295.5 B; 424/251; 424/258; 424/266
[51] Int. Cl.² ....................................... C07D 213/55
[58] Field of Search ............................. 260/295.5 R

[56] References Cited
UNITED STATES PATENTS

| | | | |
|---|---|---|---|
| 3,855,231 | 12/1974 | Meyer et al................ | 260/294.8 G |
| 3,860,601 | 1/1975 | Meyer et al................ | 260/295.5 R |
| 3,862,161 | 1/1975 | Bossert et al.............. | 260/295.5 R |

*Primary Examiner*—Alan L. Rotman

[57] ABSTRACT

1,4-Dihydropyridines bearing carboxy functions in the 3-, 5- and 6- or 2-, 3-, 5- and 6-positions and being substituted in the 4-position by phenyl, substituted phenyl, naphthyl, phenylalkyl or a heterocyclic group are antihypertensive agents and coronary vessel dilators. The compounds, of which 2-methyl-4-(3-nitrophenyl)-1,4-dihydropyridine-3,5,6-tricarboxylic acid triethylester is a representative embodiment, are prepared through condensation of an enamine with an ylidene acid ester, the latter being separately prepared or prepared in situ.

8 Claims, No Drawings

3,5,6-TRICARBOXY-4-PYRIDYL-1,4-DIHYDROPYRIDINE DERIVATIVES

This is a division of application Ser. No. 399,850 filed Sept. 24, 1973, now U.S. Pat. No. 3,905,983 granted Sept. 16, 1975.

The present invention relates to certain new dihydropyridine-polyester compounds, to a process for their production, and to their medicinal use, especially as coronary agents.

It is already known that 1,4-dihydropyridines possess interesting pharmacological properties. F. Bossert and W. Vater, Die Naturwissenschaften (1971), 58th year, issue 11, 578.

This invention provides compounds which are dihydropyridine-polyesters of the following general formula and their salts:

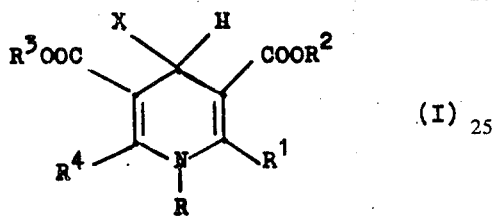

(I)

in which

R is a hydrogen atom or a linear or branched, saturated or unsaturated aliphatic radical;

$R^1$ is a hydrogen or a linear or branched alkyl radical or a $-C_nH_{2n}COOR^5$ radical in which $R^5$ is a hydrogen or alkyl radical and n is 0, 1, 2 or 3;

$R^2$ and $R^3$ are identical or different radicals consisting of a straight, branched or cyclic, saturated or unsaturated hydrocarbon chain optionally carrying 1 or 2 hydroxyl groups as substituents and optionally interrupted by 1 or 2 oxygen atoms in the chain;

$R^4$ is a $-C_nH_{2n}COOR^5$ radical in which $R^5$ and n are as defined above; and X is an aryl radical optionally carrying 1, 2 or 3 identical of different substituents selected from nitro, cyano, azido, alkyl, alkoxy, acyloxy, carbalkoxy, amino, acylamino, alkylamino, dialkylamino, $-SO_m$alkyl where m = 0, 1 or 2, phenyl, trifluoromethyl and halogen radicals, or a benzyl, styryl, cycloalkyl or cycloalkenyl radical, or a quinolyl, isoquinolyl, pyridyl, pyrimidyl, thenyl, furyl or pyrryl radical optionally carrying one or more substituents selected from alkyl, alkoxy, nitro and halogen radicals.

This invention also provides a process for the production of the new compounds defined above, in which:

a. an enamine of the general formula:

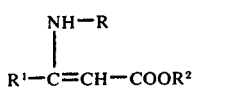 (II)

is reacted with an ylidene derivative of the general formula:

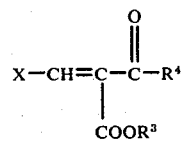 (III);

or b. an enamine of the general formula:

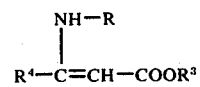 (IV)

is reacted with an ylidene derivative of the general formula:

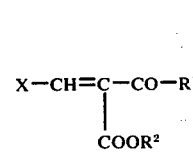 (V);

or a β-ketocarboxylic acid ester of the general formula

 (VI)

is reacted with an enamine of the general formula:

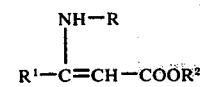 (II)

and an aldehyde of the general formula:

 (VII);

or d. a β-ketocarboxylic acid ester of the general formula:

 (VIII)

is reacted with an enamine of the general formula:

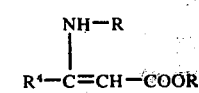 (IV)

and an aldehyde of the general formula:

 (VII)

or e. for compounds in which $R^1$ is identical to $R^4$ and $R^2$ is identical to $R^3$, two molar parts of a β-ketocarboxylic acid ester of the general formula:

 (VI)

are reacted with one molar part of an amine of the general formula:

H₂NR     (IX)

or a salt thereof, and with one part of an aldehyde of the general formula:

X-CHO     (VII)

The new free dihydropyridine polyesters of the general formula I and their salts can be interconverted in any suitable way; methods for such interconversion are known in the art.

The above five variations (a) to (e) of the process of the invention will hereinafter be referred to as Process Variants (a) to (e).

In Process Variant (a) the enamine of general formula II is preferably produced in a prior step by reacting a β-ketocarboxylic acid ester of the general formula:

R¹-CO-CH₂-COOR²     (VIII)

with an amine of the general formula:

H₂NR     (IX)

or a salt thereof.

The enamine of general formula II can be isolated and optionally purified before being reacted with the ylidene derivative of general formula III, but is preferably reacted with the said ylidene derivative without intermediate isolation and, if desired, in situ.

In Process Variant (b) the enamine of general formula IV is preferably produced in a prior step by reacting a β-ketocarboxylic acid ester of the general formula:

R⁴-CO-CH₂-COOR³     (VI)

with an amine of the general formula:

H₂NR     (IX)

or a salt thereof.

The enamine of general formula IV can be isolated and optionally purified before being reacted with the ylidene derivative of general formula V, but is preferably reacted with the said ylidene derivative without intermediate isolation and, if desired, in situ.

In all the above general formulae II to IX, R, R¹, R², R³, R⁴ and X are as defined above. Preferred meanings for these symbols are given below.

Throughout the remainder of this Specification the expression "compounds of the invention" means both the dihydropyridine-polyesters of general formula I and their salts.

Surprisingly, the compounds according to the invention possess a very strong coronary action. They can easily be converted, by saponification, into the mono-carboxylic acids or bicarboxylic acids, which are also active and are water-soluble in the form of salts, and because of their reactive ester or carboxyl groups they are also suitable for the preparation of further, pharmacologically interesting, preparations. The compounds according to the invention thus represent an enrichment of pharmacy. a. If for example 3-methoxybenzylidene-acetonedicarboxylic acid dimethyl ester, aceto-acetic acid methyl ester and methylamine (or methylaminocrotonic acid methyl ester (II)) are used as starting compounds, the course of the reaction for Process Variant (a) can be represented by the following equation:

b. If for example 2-chlorobenzylidene-acetoacetic acid ethyl ester, acetonedicarboxylic acid diethyl ester and ammonia, or β-iminoglutaric acid ethyl ester (IV) are used as starting compounds, the course of the reaction for Process Variant (b) can be represented by the following equation:

c. If for example 4-ethylmercaptobenzaldehyde, oxalacetic acid diethyl ester and β-aminocrotonic acid propyl ester are used as starting compounds, the course of the reaction Process Variant (c) can be represented by the following equation:

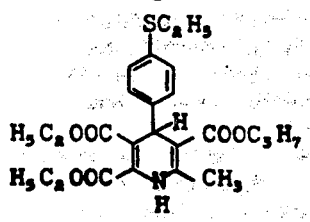

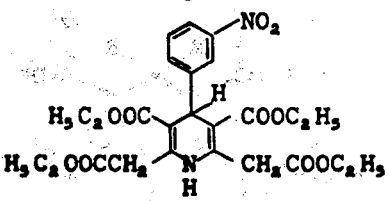

d. If for example 3-cyanobenzaldehyde, iminosuccinic acid ethyl ester and oxalacetic acid methyl ester are used as starting compounds, the course of the reaction for Process Variant (d) can be represented by the following equation:

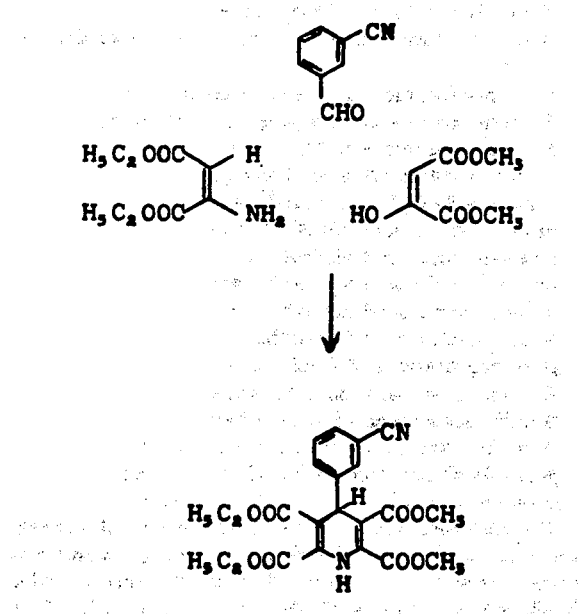

e. If for example 3-nitrobenzaldehyde, 2 parts of acetodicarboxylic acid diethyl ester and ammonia are used, the course of the reaction for Process Variant (e) can be represented by the following equation:

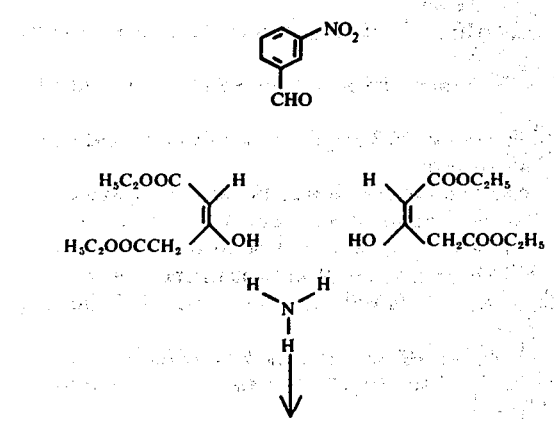

In the compounds of the invention, as represented by general formula I, and in the starting compounds of the process of the invention, as represented by the general formulae II to IX:

R preferably represents a hydrogen atom or an alkyl or alkenyl radical with up to 4 carbon atoms, especially with up to 3 carbon atoms;

$R^1$ preferably represents a hydrogen atom or a straight-chain or branched alkyl radical with 1 to 4 carbon atoms (especially 1 to 2 carbon atoms) or a -$(CH_2)_n$-CO.$OR^5$ radical (in which $R^5$ represents a hydrogen atom or an alkyl radical with 1 to 4 carbon atoms and n represents 0, 1, 2 or 3);

$R^2$ preferably represents a radical consisting of a saturated or ethylenically unsaturated aliphatic hydrocarbon chain with up to 6 carbon atoms, optionally carrying a hydroxyl group as substituent, and optionally interrupted by an oxygen atom in the chain;

$R^3$ preferably represents a saturated or unsaturated hydrocarbon radical with up to 6 carbon atoms;

$R^4$ preferably represents a -$(CH_2)_n$-CO.$OR^5$ radical (in which $R^5$ represents a hydrogen atom or an alkyl radical with 1 to 4 carbon atoms and n represents 0, 1, 2 or 3); and X preferably represents a phenyl radical optionally carrying as substituents 1 to 2 nitro groups (especially 1 nitro group), a cyano group, an azido group, 1 or 2 trifluoromethyl groups (especially 1 trifluoromethyl group), an -$SO_n$ Alkyl group (in which n represents 0 or 2 and "Alkyl" contains 1 to 4 carbon atoms), 1 or 2 alkyl groups, 1, 2 or 3 alkoxy groups, 1 or 2 acetoxy groups, 1 or 2 amino groups, 1 or 2 acetylamino groups, 1 or 2 alkylamino or dialkylamino groups (each with 1 to 4, especially 1 or 2, carbon atoms in the alkyl or alkoxy groups) or one or more chlorine, bromine, fluorine or phenyl radicals, the total number of these substituents being at most 3; or represents a pyridyl, pyrimidyl, naphthyl, quinolyl, isoquinolyl, thenyl, pyrryl or furyl radical optionally carrying as substituent an alkyl or alkoxy group (each with 1 to 4 carbon atoms, especially with 1 or 2 carbon atoms), a nitro group or a halogen atom (especially chlorine or bromine); or represents a benzyl or styryl radical or a cycloalkyl or cycloalkenyl radical with 5 to 6 carbon atoms.

A particularly preferred group are compounds of the formula:

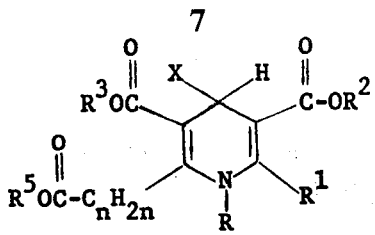

wherein R is hydrogen, lower alkyl, lower alkenyl or lower alkynyl;
R¹ is lower alkyl or

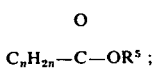

each of R² and R³, taken independently of the other, is lower alkyl, hydroxy lower alkyl, lower alkoxy(-lower alkyl), lower alkenyl or lower alkynyl;
R⁵ is hydrogen or lower alkyl; and
X is phenyl; substituted phenyl in which the substituents are one to three members selected from the group consisting of lower alkyl, lower alkoxy, halogeno, nitro, cyano, trifluoromethyl, azido, carbo(lower alkoxy), lower alkanoyl, lower alkylsulfonyl, lower alkylsulfinyl, lower alkylthio and phenyl; naphthyl; phenyl (lower alkyl); or a heterocyclic ring selected from the group consisting of quinolyl, isoquinolyl, pyridyl, thenyl, furyl and pyrryl, said heterocyclic ring being unsubstituted or substituted by one or two members selected from the group consisting of lower alkyl, lower alkoxy and halogeno; and
n has a value of 0 to 5;
and the pharmaceutically acceptable salts thereof with bases.

Among the new dihydropyridine-polyester salts of the invention, those salts that are pharmaceutically acceptable are especially important and are preferred.

The β-ketocarboxylic acid esters of general formula VIII which can be used as starting compounds in the process according to the invention are known or can be produced by known processes (Pohl, Schmidt, U.S. Pat. No. 2,351,366).

As examples of such esters there may be mentioned:
formylacetic acid ethyl ester,
formylacetic acid butyl ester,
acetoacetic acid methyl ester,
acetoacetic acid ethyl ester,
acetoacetic acid propyl ester,
acetoacetic acid isopropyl ester,
acetoacetic acid butyl ester,
acetoacetic acid t-butyl ester,
acetoacetic acid (α- and β-)-hydroxyethyl esters,
acetoacetic acid (α- and β-)-methoxyethyl esters,
acetoacetic acid (α- and β-)-ethoxyethyl esters,
acetoacetic acid (α- and β-)-n-propoxyethyl esters,
acetoacetic acid allyl ester,
acetoacetic acid propargyl ester,
acetoacetic acid cyclohexyl ester,
propionylacetic acid ethyl ester, butyrylacetic acid ethyl ester
isobutyrylacetic acid ethyl ester
oxalacetic acid dimethyl ester,
oxalacetic acid diethyl ester,
oxalacetic acid diisopropyl ester,
acetonedicarboxylic acid dimethyl ester,
acetonedicarboxylic acid diethyl ester,
acetonedicarboxylic acid dibutyl ester and
β-keto-adipic acid diethyl ester.

The amines of general formula IX which can be used as starting compounds according to the invention are already known.

As examples there may be mentioned: ammonia, methylamine, ethylamine, propylamine, butylamine, isopropylamine, isobutylamine and allylamine.

The enamine-β-ketocarbonyl compounds of general formula II which can be used as starting compounds according to the invention are known or can be produced by known methods from the corresponding β-diketo compounds (A.C. Cope, J.A.C.S. 67, 1,017 (1945)).

As examples of these compounds there may be mentioned:
β-aminocrotonic acid methyl ester,
β-aminocrotonic acid ethyl ester,
β-aminocrotonic acid isopropyl ester,
β-aminocrotonic acid butyl ester,
β-aminocrotonic acid (α- and β-)-methoxyethyl esters,
β-aminocrotonic acid β-ethoxyethyl ester,
β-aminocrotonic acid β-propoxyethyl ester,
β-aminocrotonic acid t-butyl ester,
β-aminocrotonic acid cyclohexyl ester,
β-amino-β-ethylacrylic acid ethyl ester,
iminosuccinic acid dimethyl ester,
iminosuccinic acid diethyl ester,
iminosuccinic acid dipropyl ester,
iminosuccinic acid dibutyl ester,
β-iminoglutaric acid dimethyl ester,
β-iminoglutaric acid diethyl ester,
β-iminoadipic acid dimethyl ester,
β-iminoadipic acid diisopropyl ester,
β-methyl-aminocrotonic acid methyl ester,
β-ethylaminocrotonic acid ethyl ester and
β-methyliminoglutaric acid diethyl ester.

The ylidene-β-ketocarboxylic acid esters of general formula III which can be used as starting compounds according to the invention either are known or can be produced by known methods (Org. Reactions XV, 204 et seq., (1967)).

As examples of these esters there may be mentioned:
benzylideneoxalacetic acid dimethyl ester,
2-nitrobenzylideneoxalacetic acid diethyl ester,
3-nitrobenzylideneoxalacetic acid diethyl ester,
2-cyanobenzylideneoxalacetic acid dipropyl ester,
3,4-dihydroxymethylbenzylideneoxalacetic acid dimethyl ester,
3,4,5-trimethoxybenzylideneoxalacetic acid diisopropyl ester,
2-methylmercaptobenzylideneoxalacetic acid dipropyl ester,
2-trifluoromethylbenzylideneoxalacetic acid diethyl ester,
3-trifluoromethylbenzylideneoxaldiacetic acid dimethyl ester,
2-chlorobenzylideneoxalacetic acid propyl ester,
3-chlorobenzylideneoxalacetic acid dibutyl ester,
3-ethoxybenzylideneoxalacetic acid methyl ester,
3-azidobenzylideneoxalacetic acid ethyl ester,
4-carboxyethylbenzylideneoxalacetic acid dimethyl ester,
2-furylmethylideneoxalacetic acid diethyl ester,
4-nitrobenzylidene-β-ketoglutaric acid dimethyl ester and 4-methoxybenzylidene-β-ketoglutaric acid diethyl ester.

The β-ketocarboxylic acid esters of general formula VI and the enamino-β-ketocarboxylic acid esters of general formula IV which can be used as starting compounds according to the invention, are already known or can, as mentioned in the case of the compounds of the general formulae VIII and II respectively, be manufactured according to known processes.

As examples there may be mentioned
β-Dicarbonyl compounds of general formula VI:
Oxalacetic acid dimethyl ester,
oxalacetic acid diethyl ester,
oxalacetic acid isopropyl ester,
acetonedicarboxylic acid dimethyl ester,
acetonedicarboxylic acid diethyl ester,
acetonedicarboxylic acid dibutyl ester and
β-ketoadipic acid diethyl ester.

Imino-dicarboxylic acid diesters of general formula IV:
Iminosuccinic acid dimethyl ester,
iminosuccinic acid diethyl ester,
iminosuccinic acid dipropyl ester,
iminosuccinic acid dibutyl ester,
β-iminoglutaric acid dimethyl ester,
β-iminoglutaric acid diethyl ester,
β-iminoadipic acid dimethyl ester,
β-iminoadipic acid diisopropyl ester
methyliminosuccinic acid diisopropyl ester,
ethyliminosuccinic acid diethyl ester and
β-isopropyliminoglutaric acid dipropyl ester.

The ylidene-β-ketocarboxylic acid esters of general formula V which can be used according to the invention either are known or can, as mentioned for compounds of the general formula III, be produced by known methods.

As examples of such ylidene-β-ketocarboxylic acid esters there may be mentioned:
Benzylideneacetoacetic acid methyl ester,
2'-nitrobenzylideneacetoacetic acid methyl ester,
3'-nitrobenzylideneacetoacetic acid propargyl ester,
3'-nitrobenzylideneacetoacetic acid allyl ester,
3'-nitrobenzylideneacetoacetic acid β-methoxyethyl ester,
3'-nitrobenzylideneacetoacetic acid β-ethoxyethyl ester,
3'-nitrobenzylideneacetoacetic acid isopropyl ester,
4'-nitrobenzylideneacetoacetic acid n-propyl ester,
3'-nitro-6'-chlorobenzylideneacetoacetic acid methyl ester,
2'-cyanobenzylideneacetoacetic acid methyl ester,
2'-cyanobenzylideneacetoacetic acid ethyl ester,
2'-cyanobenzylidenepropionylacetic acid ethyl ester,
3'-cyanobenzylideneacetoacetic acid methyl ester,
3'-nitro-4'-chlorobenzylideneacetoacetic acid t-butyl ester,
3'-nitro-4'-chlorobenzylideneacetoacetic acid methyl ester,
2'-nitro-4'-methoxybenzylideneacetoacetic acid methyl ester,
2'-cyano-4'-methylbenzylideneacetoacetic acid ethyl ester,
2'-azidobenzylideneacetoacetic acid ethyl ester,
2'-methylmercaptobenzylideneacetoacetic acid methyl ester,
2'-methylmercaptobenzylideneacetoacetic acid isopropyl ester,
2'-sulphinylmethylbenzylideneacetoacetic acid ethyl ester,
2'-sulphonylmethylacetoacetic acid allyl ester,
4-sulphonylmethylacetoacetic acid ethyl ester,
(1'-naphthylidene)-acetoacetic acid methyl ester,
(1'-naphthylidene)-acetoacetic acid ethyl ester,
(2'-naphthylidene)-acetoacetic acid ethyl ester,
(2'-ethoxy-1'-naphthylidene)-acetoacetic acid methyl ester,
(2'-methoxy-1'-naphthylidene)-acetoacetic acid ethyl ester,
5'-bromo-(1'-naphthylidene)-acetoacetic acid methyl ester,
(2'-quinolyl)-methylideneacetoacetic acid ethyl ester,
(3'-quinolyl)-methylideneacetoacetic acid methyl ester,
(4'-quinolyl)-methylideneacetoacetic acid ethyl ester,
(8'-quinolyl)-methylideneacetoacetic acid ethyl ester,
(1'-isoquinolyl)-methylideneacetoacetic acid methyl ester,
(3'-isoquinolyl)-methylideneacetoacetic acid methyl ester,
α-pyridylmethylideneacetoacetic acid methyl ester,
α-pyridylmethylideneacetoacetic acid ethyl ester,
α-pyridylmethylideneacetoacetic acid allyl ester,
α-pyridylmethylideneacetoacetic acid cyclohexyl ester,
β-pyridylmethylideneacetoacetic acid β-methoxyethyl ester,
γ-pyridylmethylideneacetoacetic acid methyl ester,
6-methyl-α-pyridylmethylideneacetoacetic acid ethyl ester,
4',6'-dimethoxy-(5'-pyrimidyl)-methylideneacetoacetic acid ethyl ester,
(2'-thenyl)-methylideneacetoacetic acid ethyl ester,
(2'-furyl)-methylideneacetoacetic acid allyl ester,
(2'-pyrryl)-methylideneacetoacetic acid methyl ester,
3'-nitrobenzylidenepropionylacetic acid ethyl ester,
α-pyridylmethylidenepropionylacetic acid methyl ester,
2'-, 3'- and 4'-methoxybenzylideneacetoacetic acid ethyl esters,
2'-methoxybenzylideneacetoacetic acid allyl ester,
2'-methoxybenzylideneacetoacetic acid propargyl ester,
2'-methoxybenzylidene-β-methoxyethyl ester,
2'-isopropoxybenzylideneacetoacetic acid ethyl ester,
3'-butoxybenzylideneacetoacetic acid methyl ester,
3',4',5'-trimethoxybenzylideneacetoacetic acid allyl ester,
2'-methylbenzylidenepropionylacetic acid methyl ester,
2'-, 3'- and 4'-methylbenzylideneacetoacetic acid ethyl esters,
2'-methylbenzylideneacetoacetic acid β-methoxyethyl ester,
2'-methylbenzylideneacetoacetic acid β-propoxyethyl ester,
3',4'-dimethoxy-5'-bromobenzylideneacetoacetic acid ethyl ester,
2'-, 3'- and 4'-chloro/bromo/fluorobenzylideneacetoacetic acid ethyl esters,
2'-fluorobenzylideneacetoacetic acid methyl ester, 3'-chlorobenzylidenepropionylacetic acid ethyl ester,
3'-chlorobenzylideneacetoacetic acid ethyl ester,
2'-chlorobenzylideneacetoacetic acid allyl ester,
2'-, 3'- and 4'-trifluoromethylbenzylideneacetoacetic acid propyl ester,
2'-trifluoromethylbenzylideneacetoacetic acid isopropyl ester,
3'-trifluoromethylbenzylideneacetoacetic acid methyl ester,
2'-carboethoxybenzylideneacetoacetic acid ethyl ester,
3'-carboxymethylbenuylideneacetoacetic acid methyl ester,
4-carboxyisopropylbenzylideneacetoacetic acid isopropyl ester and
4'-carboxymethylbenzylideneacetoacetic acid allyl ester.

The aldehydes of general formula VII which can be used according to the invention either are already known or can be produced by known methods (E. Mosettig, Org. Reactions, VIII, 218 et seq., (1954)).

As examples of these aldehydes there may be mentioned: Benzaldehyde,
2-, 3- and 4-methoxybenzaldehyde,
2-isopropoxybenzaldehyde,
3-butoxybenzaldehyde,
3,4-dihydroxymethylenebenzaldehyde,
3,4,5-trimethoxybenzaldehyde,
2-, 3- and 4-chloro/bromo/fluorobenzaldehyde,
2,4- and 2,6-dichlorobenzaldehyde,
2,4-dimethylbenzaldehyde,
3,5-diisopropyl-4-methoxybenzaldehyde,
2-, 3- and 4-nitrobenzaldehydes,
2,4- and 2,6-dinitrobenzaldehydes,
2-nitro-6-bromobenzaldehyde,
2-nitro-3-methoxy-6-chlorobenzaldehyde,
2-nitro-4-chlorobenzaldehyde,
2-nitro-4-methoxybenzaldehyde,
2-, 3- and 4-trifluoromethylbenzaldehydes,
2-, 3- and 4-dimethylaminobenzaldehydes,
4-dibutylaminobenzaldehyde,
4-acetoaminobenzaldehyde,
2-, 3- and 4-cyanobenzaldehydes,
2-nitro-4-cyanobenzaldehyde,
3-chloro-4-cyanobenzaldehyde,
2-, 3- and 4-methylmercaptobenzaldehydes,
2-methylmercapto-5-nitrobenzaldehyde,
2-butylmercaptobenzaldehyde,
2-, 3- and 4-methylsulphinylbenzaldehydes,
2-, 3- and 4-methylsulphonylbenzaldehydes,
benzaldehyde-2-carboxylic acid ethyl ester,
benzaldehyde-3-carboxylic acid isopropyl ester,
benzaldehyde-4-carboxylic acid butyl ester,
3-nitrobenzaldehyde-4-carboxylic acid ethyl ester,
cinnamaldehyde,
hydrocinnamaldehyde,
formylcyclohexane,
1-formylcyclohex-3-ene,
1-formylcyclohex-1,3-ine,
1-formylcyclopent-3-ene,
α-, β- and γ-pyridinaldehydes,
6-methylpyridin-2-aldehyde,
furan-2-aldehyde,
thiophen-2-aldehyde,
pyrrol-2-aldehyde,
2-, 3- and 4-azido-benzaldehydes,
pyrimidin-4-aldehyde,
5-nitro-6-methylpyridin-2-aldehyde,
1- and 2-naphthaldehydes,
5-bromo-1-naphthaldehyde,
quinolin-2-aldehyde,
7-methoxy-quinolin-4-aldehyde and
iso-quinolin-1-aldehyde.

Possible diluents are water and (in principle) all inert organic solvents. Preferred organic solvents include alcohols (such as ethanol, methanol and isopropanol), ethers (such as dioxane and diethyl ether), glacial acetic acid, dimethylformamide, dimethylsulphoxide, acetonitrile and pyridine.

The reaction temperatures can be varied over a substantial range. In general, the reaction is carried out between 20° and 150°C, preferably at the boiling point of the diluent.

The reaction can be carried out under normal pressure but also under elevated pressure. In general, normal pressure is used.

In carrying out the process according to the invention, the compounds participating in the reaction are generally each employed in approximately molar amounts, except for the amine or its salt, which is appropriately added in an excess of 1 to 2 mols.

The 1,4-dihydropyridine-monocarboxylic acids or -dicarboxylic acids (for example $R^5 = H$) can be obtained by alkaline or acid hydrolysis of the corresponding esters.

Additionally to the compounds described in the Preparative Examples, the following may be mentioned individually as new active compounds of the invention:

1,2-dimethyl-4-(3'-methoxyphenyl)-1,4-dihydropyridine-3,5,6-tricarboxylic acid tripropyl ester;

1-methyl-2-ethyl-4-(2'-chlorophenyl)-1,4-dihydropyridine-3,5,6-tricarboxylic acid 3-β-ethoxyethyl ester-5,6-dimethyl ester;

1-propyl-4-(2'-nitro-5-thenyl)-1,4-dihydropyridine-2,3,5,6-tetracarboxylic acid tetraethyl ester;

2-propyl-4-(4-pyrimidyl)-1,4-dihydropyridine-3,5,6-tricarboxylic acid 3-isopropyl ester-5,6-dimethyl ester;

4-styryl-1,4-dihydropyridine-2,3,5,6-tetracarboxylic acid tetrapropyl ester;

2-isopropyl-4-(4'-quinolyl)-1,4-dihydropyridine-3,5,6-tricarboxylic acid triisopropyl ester;

4-(2'-bromo-5-furyl)-1,4-dihydropyridine-2,3,5,6-tetracarboxylic acid tetrabutyl ester;

2-ethyl-4-(2'-cyanophenyl)-1,4-dihydropyridine-3,5,6-tricarboxylic acid 3-ethyl ester-5,6-dimethyl ester;

4-(naphthyl-1')-1,4-dihydropyridine-3,5-dicarboxylic acid diethyl ester-2,6-diacetic acid diethyl ester;

4-(3'-nitro-6'-chlorophenyl)-1,4-dihydropyridine-2,3,5,6-tetracarboxylic acid tetramethyl ester;

2-methyl-4-(3'-trifluoromethylphenyl)-1,4-dihydropyridine-3,5-dicarboxylic acid diethyl ester-6-acetic acid ethyl ester;

1-methyl-4-(3'-cyanophenyl)-1,4-dihydropyridine-2,3,5,6-tetracarboxylic acid tetramethyl ester;

4-(3',4',5'-trimethoxyphenyl)-1,4-dihydropyridine-3,5-dicarboxylic acid diethyl ester-2,6-diacetic acid diethyl ester;

4-(3'-nitrophenyl)-1,4-dihydropyridine-2,3,5,6-tetracarboxylic acid tetrapropargyl ester;

4-(3'-chlorophenyl)-1,4-dihydropyridine-3,5-dicarboxylic acid dimethyl ester-2,6-diacetic acid dimethyl ester; and 2-methyl-4-(2'-nitro-5'-trifluoromethyl)-1,4-dihydropyridine-3,5,6-tricarboxylic acid 3-isopropyl ester-5,6-diethyl ester.

The new compounds can be used as drugs, especially to influence the circulation; those that are free acids form readily water-soluble salts with bases and then do not require a solubilising agent.

The compounds according to the invention have a broad and diverse pharmacological action spectrum.

In detail, the following main actions were demonstrable in animal experiments:

1. On parenteral, oral and perlingual admimistration the compounds produce a distinct and long-lasting dilation of the coronary vessels. This action on the coronary vessels is intensified by a simultaneous nitrite-like effect of reducing the load on the heart. The compounds of the invention influence or modify the heart metabolism in the sense of an energy saving.

2. The compounds of the invention lower the blood pressure of normotonic and hypertonic animals and can thus be used as anti-hypertensive agents.

3. The excitability of the stimulus formation and excitation conduction system within the heart is lowered, so that an anti-fibrillation action demonstrable at therapeutic doses results.

4. The tone of the smooth muscle of the vessels is (such as, for example, the central nervous system).

5. The compounds of the invention have strongly muscular-spasmolytic actions which manifest themselves on the smooth muscle of the stomach, the intestinal tract, the urogenital tract and the respiratory system.

6. The compounds of the invention influence the cholesterol level and lipid level of the blood.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention either alone or in admixture with a diluent.

The invention also provides a medicament in the form of tablets (including lozenges and granules), dragees, capsules, pills, ampoules or suppositories comprising a compound of the invention either alone or in admixture with the diluent.

"Medicament" as used in this Specification means physically discrete coherent portions suitable for medical administration. "Medicament in dosage unit form" as used in this Specification means physically discrete coherent portions suitable for medical administration each containing a daily dose or a multiple (up to four times) a sub-multiple (down to a fortieth) of a daily dose of the compound of the invention. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granules or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), mircocrystalline cellulose, aluminium metahydroxide, bentonite, agar-agar and tragacanth or mixture thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.5–90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention (whether in dosage unit form or not) may be, for example, any of the following: tablets, (including lozenges and granules), pills, dragees, capsules (especially oral-release capsules), suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 0.25–900 mg, especially 1–450 mg., of active ingredient; the preferred daily dose for peroral administration is 5 mg. – 4.5 g., especially 50 mg. – 2.7 g. of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the abovementioned diseases in human and non-human animals, which comprises administering to the animals a compound of the invention alone or in admixture with a diluent or in the form of a medicament according to the invention.

It is envisaged that these active compounds will be administered in the customary manner for coronary-active compounds, preferably perorally or parenterally, especially perlingually or intravenously. Preferred pharmaceutical compositions and medicaments are therefore those adapted for peroral (especially perlingual) and intravenous administration, such as tablets, oral-release capsules, and ampoules of injectable solution. Administration in the method of the invention is preferably peroral or intravenous.

In general it has proved advantageous, in the case of intravenous administration, to administer amounts of 0.005 to 10 mg/kg, preferably 0.02 to 5 mg/kg, of body weight daily to achieve effective results, whilst in the case of oral administration the dosage is 0.1 to 50 mg/kg, preferably 1 to 30 mg/kg of body weight daily.

Nevertheless it can at times be necessary to deviate from the amounts mentioned and in particular to do so as a function of the body weight of the test animal or of the nature of the administration route, but also because of the type of animal and its individual behaviour towards the medicine or the nature of its formulation and the time or interval at which it is administered. Thus it may suffice, in some cases, to manage with less than the abovementioned minimum amount whilst in other cases the upper limit mentioned must be exceeded. Where major amounts are administered it can be advisable to divide these into several individual administrations over the course of the day. The same dosage range is envisaged for administration in human medicine.

The coronary action of the compounds according to the invention can be demonstrated in vivo, as for example in narcotised heart-catheterised mongrel dogs by measuring the rise in oxygen saturation in the coronary sinus, as shown in Table I. The dose quoted is the minimum intravenous dose required (expressed in mg. active compound per kg. body weight) to cause a clearly recognizable rise in the oxygen saturation in the coronary sinus.

Table I

| Compound of Example No.: | Dose (mg/kg intravenous) | Duration of effect (minutes) |
|---|---|---|
| 1 | 2 | 30 |
| 2 | 3 | 20 |
| 3 | 5 | 20 |
| 5 | 1 | 45 |
| 6 | 5 | 10 |
| 9 | 5 | 30 |
| 11 | 3 | 20 |
| 12 | 0.1 | 30 |
| 13 | 2 | 60 |
| 20 | 5 | 20 |
| 23 | 10 | 20 |
| 26 | 0.5 | 60 |
| 28 | 5 | 20 |
| 31 | 5 | 10 |
| 33 | 10 | 10 |
| 34a | 5 | 20 |
| 36 | 5 | 3 |
| 37 | 10 | 20 |
| 38 | 10 | 20 |
| 41 | 2 | 20 |
| 43 | 3 | 10 |

EXAMPLE 1

2-Methyl-4-(α-pyridyl)-1,4-dihydropyridine-3,5-dicarboxylic acid dimethyl ester-6-acetic acid methyl ester

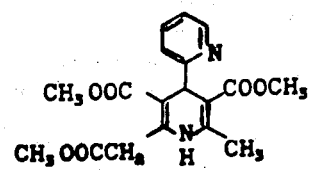

a. After heating a solution of 10.5 ccs of pyridin-2-aldehyde, 11.6 g of acetoacetic acid methyl ester and 17.3 g of β-iminoglutaric acid dimethyl ester in 50 ccs of ethanol under reflux for several hours and subsequent cooling, light grey crystals of melting point 165° (ethanol) are obtained. Yield 60%.

b. After heating a solution of 10.5 ccs of pyridin-2-aldehyde, 17.4 g of acetonedicarboxylic acid dimethyl ester and 11.6 g of β-aminocrotonic acid methyl ester in 50 ccs of ethanol for several hours, and cooling, light grey crystals of melting point 165° are obtained. Yield 57%.

EXAMPLE 2

2-Methyl-4-(α-pyridyl)-1,4-dihydropyridine-3,5,6-tricarboxylic acid 3-methyl ester-5,6-diethyl ester

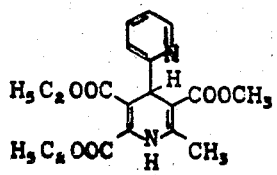

10.5 ccs of pyridin-2-aldehyde, 11.6 g of β-aminocrotonic acid methyl ester and 19 g of oxalacetic acid diethyl ester in 60 ccs of ethanol are heated for several hours under reflux and cooled, and light yellow crystals of melting point 142°–143° (ethanol) are obtained. Yield 62%.

EXAMPLE 3

2-Methyl-4-(β-pyridyl)-1,4-dihydropyridine-3,5,6-tricarboxylic acid triethyl ester

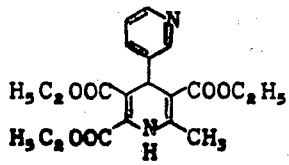

10.5 ccs of pyridin-3-aldehyde, 13 g of β-amino-crotonic acid ethyl ester and 19 g of oxalacetic acid diethyl ester in 60 ccs of ethanol are heated to the boil overnight and cooled, and after filtration light yellow crystals of melting point 127°–129° (ethanol) are obtained. Yield 75%.

EXAMPLE 4

2-Methyl-4-(γ-pyridyl)-1,4-dihydropyridine-3,5,6-tricarboxylic acid triethyl ester

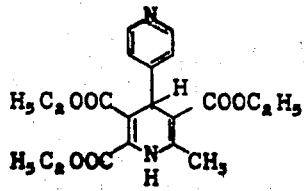

A solution of 10.5 ccs of pyridin-4-aldehyde, 13 g of β-aminocrotonic acid ethyl ester and 19 g of oxalacetic acid diethyl ester in 60 ccs of ethanol is heated to the boil for several hours and subsequently cooled, and the product is filtered off. Yellowish-orange crystals of melting point 135°. Yield 50%.

EXAMPLE 5

2-Methyl-4-(α-pyridyl)-1,4-dihydropyridine-3,5,6-tricarboxylic acid triethyl ester

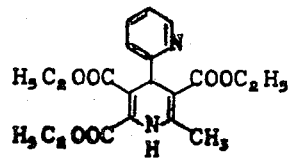

After heating a solution of 10.5 ccs of pyridin-2-aldehyde, 13 g of β-aminocrotonic acid ethyl ester and 19 g of oxalacetic acid diethyl ester in 60 ccs of ethanol under reflux for 8 hours, the mixture is cooled and the product is filtered off. Yellow crystals of melting point 138° (ethanol). Yield 75%.

EXAMPLE 6

4-(α-Pyridyl)-1,4-dihydropyridine-3,5-dicarboxylic acid diethyl ester-2,6-diacetic acid diethyl ester

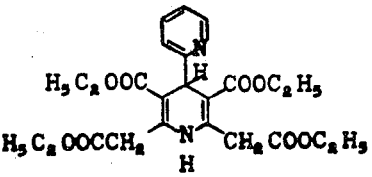

After heating a solution of 10.5 g of pyridin-2-aldehyde, 17.3 g of iminoglutaric acid diethyl ester and 17.4 g of acetonedicarboxylic acid diethyl ester in 60 ccs under reflux for several hours, and cooling, biege crystals of melting poing 134° are obtained. Yield 35%.

EXAMPLE 7

4-(3'-Nitrophenyl)-1,4-dihydropyridine-3,5-dicarboxylic acid dimethyl ester-1,6-diacetic acid dimethyl ester

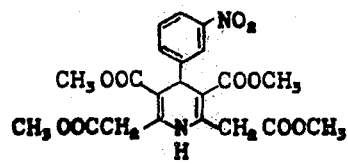

After heating a solution of 15 g of 3-nitrobenzaldehyde, 17.3 g of acetdicarboxylic acid dimethyl ester and iminosuccinic acid dimethyl ester in 60 ccs of ethanol under reflux for 6 hours, the mixture is evaporated. An oil is obtained.

EXAMPLE 8

4-(2'-Nitrophenyl)-1,4-dihydropyridine-2,3,5,6-tetracarboxylic acid tetraethyl ester

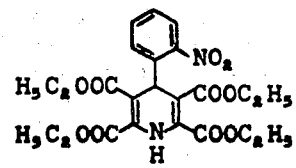

A solution of 7.5 g of o-nitrobenzaldehyde, 9.5 g of oxalacetic acid diethyl ester and 9.4 g of iminosuccinic acid diethyl ester in 30 ccs of alcohol is heated under reflux overnight and subsequently cooled. After filtration, light yellow crystals of melting point 109° (ethanol) are obtained. Yield 58%.

EXAMPLE 9

4-(2'-Trifluoromethylphenyl-1,4-dihydropyridine-2,3,5,6-tetracarboxylic acid ethyl ester

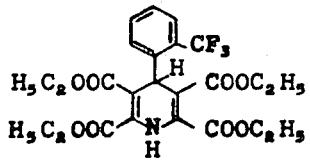

A solution of 8.7 g of 2-trifluoromethylbenzaldehyde, 9.4 g of iminosuccinic acid diethyl ester and 9.5 g of oxalacetic acid ethyl ester in 30 ccs of ethanol is heated to the boil overnight and cooled, and the product is filtered off and rinsed with alcohol. Yellow crystals of melting point 118° (ethanol). Yield 55%.

EXAMPLE 10

4-(2'-Trifluoromethylphenyl)-1,4-dihydropyridine-2-methyl-3,5-dicarboxylic acid diethyl ester-6-carboxylic acid.

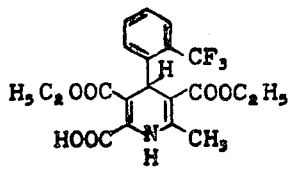

17.4 g of 2-trifluoromethylbenzaldehyde, 13 g of β-aminocrotonic acid ethyl ester and 19 g of oxalacetic acid diethyl ester in 50 ccs of alcohol are heated to the boil for 6–8 hours, a solution of 2.3 g of sodium in 300 ccs of alcohol is added and the mixture is heated under reflux for a further 5–8 hours. It is then evaporated in vacuo, the residue is taken up in hot water (animal charcoal) and after filtration the product is precipitated with dilute sulphuric acid. Yellow crystals of melting point 138°–140° from ether. Yield 55%.

EXAMPLE 11

4-(β-Pyridyl)-1,4-dihydropyridine-3,5-dicarboxylic acid diethyl ester-2,6-diacetic acid diethyl ester.

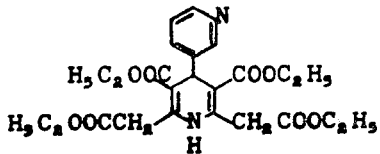

A solution of 5.2 ccs of pyridin-3-aldehyde, 10 g of β-iminoglutaric acid diethyl ester and 10 g of acetonedicarboxylic acid diethyl ester in 40 ccs of ethanol is heated to the boil for several hours and the crystals obtained after prolonged cooling are filtered off. Light beige crystals of melting point 129°–130° (benzene-ligroin). Yield 60%.

EXAMPLE 12

2-Methyl-4-(3'-nitrophenyl)-1,4-dihydropyridine-3,5,6-tricarboxylic acid triethyl ester.

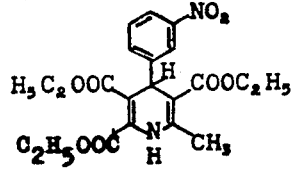

15 g of 3-nitrobenzaldehyde, 13 g of β-aminocrotonic acid ethyl ester and 19 g of oxalacetic acid diethyl ester in 60 ccs of ethanol are heated to the boil overnight. The green-yellow crystals obtained, in 62% yield, after cooling, melt at 123°.

EXAMPLE 13

2-Methyl-4-(3'-nitrophenyl)-1,4-dihydropyridine-3,5-dicarboxylic acid diethyl ester-6-carboxylic acid.

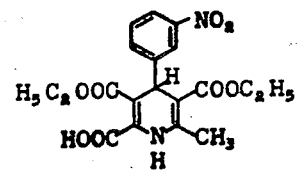

43 g of the triester (Example 12), in a solution of 2.3 g of sodium in 500 ccs of alcohol, are heated to the boil for several hours, the mixture is concentrated in vacuo, the residue is taken up in warm water and after filtration the product is precipitated with dilute sulphuric acid. Yellow crystals of melting poing 156° from ethanol. Yield 90%.

EXAMPLE 14

1,2-Dimethyl-4-(3'-nitrophenyl)-1,4-dihydropyridine-3-carboxylic acid methyl ester-5,6-dicarboxylic acid diethyl ester.

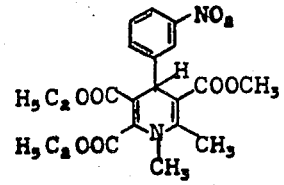

A solution of 12.5 g of 3-nitrobenzylidene-acetoacetic acid methyl ester and 10.5 g of oxalacetic acid diethyl ester and 4 g of methylamine hydrochloride in 40 ccs of pyridine is heated to 100°–110° (external temperature) for 5 hours and subsequently added to water. Beige crystals of melting point 133°, from ether. Yield 45%.

EXAMPLE 15

2-Methyl-4-(α-naphthyl)-1,4-dihydropyridine-3,5,6-tricarboxylic acid triethyl ester.

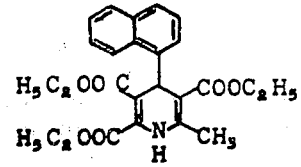

After heating a solution of 15.6 g of 1-naphthaldehyde, 19 g of oxalacetic acid diethyl ester and 13 g of β-aminocrotonic acid ethyl ester in 40 ccs of ethanol under reflux for 6–8 hours, and cooling, light yellow crystals of melting point 112° (ethanol) are obtained. Yield 65%.

EXAMPLE 16

2-Methyl-4-(α-naphthyl)-1,4-dihydropyridine-3,5-dicarboxylic acid diethyl ester-6-carboxylic acid.

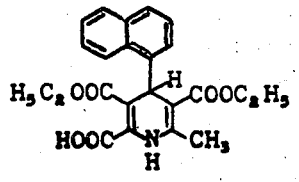

21.5 g of the triester (Example 15), in a solution of 2.15 g of sodium in 250 ccs of ethanol, are heated to the boil for approx. 6 hours, the mixture is concentrated in vacuo and the residue is taken up in warm water. After filtration, the product is precipitated with dilute sulphuric acid. Yellow crystals of melting point 177° (ether). Yield 85%.

EXAMPLE 17

2-Methyl-4-(2'-trifluoromethylphenyl)-1,4-dihydropyridine-3-carboxylic acid methyl ester-5-carboxylic acid ethyl ester-6-carboxylic acid

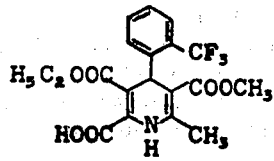

17.4 g of 2-trifluoromethylbenzaldehyde, 11.5 g of β-aminocrotonic acid methyl ester and 19 g of oxalacetic acid diethyl ester in 40 ccs of ethanol are heated to the boil overnight, a solution of 2.3 g of sodium in 250 ccs of ethanol is added and the mixture is heated under reflux for a further 5–8 hours. After working up, light yellow crystals of melting point 164° (ether) are obtained. Yield 50%.

EXAMPLE 18

2-Methyl-4-(3',4',5'-trimethoxyphenyl)-1,4-dihydropyridine-3,5,6-tricarboxylic acid triethyl ester

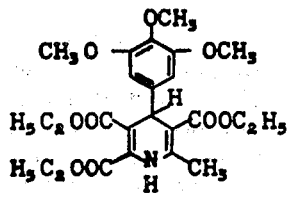

11.8 g of 3,4,5-trimethoxybenzaldehyde, 14 g of oxalacetic acid diethyl ester and 7.8 g of β-aminocrotonic acid ethyl ester in 30 ccs of ethanol are heated to the boil overnight and light yellow crystals of melting point 134° are obtained. Yield 40%.

EXAMPLE 19

2-Methyl-4-(3',4',5'-trimethoxyphenyl)-1,4-dihydropyridine-3,5-dicarboxylic acid diethyl ester-6-carboxylic acid.

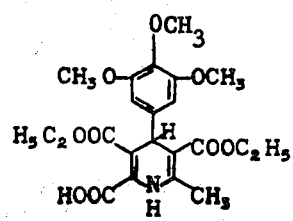

23.8 g of the triester (Example 18), in a solution of 1.15 g of sodium in 300 ccs of ethanol, are heated for several hours to the boil, and after working up yellow crystals of melting point 144° (ether) are obtained. Yield 80%.

EXAMPLE 20

2-Methyl-4-(3'-fluoro-4'-methoxyphenyl)-1,4-dihydropyridine-3,5,6-tricarboxylic acid triethyl ester.

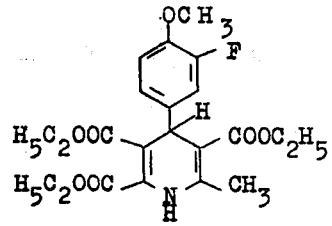

After heating a solution of 17 g of 3-fluoro-4-methoxybenzaldehyde, 20.9 g of oxalacetic acid diethyl ester and 14.3 g of β-aminocrotonic acid ethyl ester in 80 ccs of ethanol under reflux, the mixture is evaporated in vacuo and the reaction product is obtained as a light yellow oil.

EXAMPLE 21

2-Methyl-4-(3'-fluoro-4'-methoxyphenyl)-1,4-dihydropyridine-3,5-dicarboxylic acid diethyl ester-6-carboxylic acid.

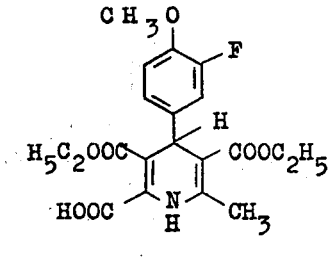

43 g of the triester obtained according to Example 20, in a solution of 2.3 g of sodium in 250 ccs of ethanol, are heated to the boil for 6–8 hours, the mixture is evaporated in vacuo, the residue is taken up in water and after filtration the product is precipitated with dilute sulphuric acid. Yellow crystals of melting point 106° (ether).

EXAMPLE 22

2-Methyl-4-(3'-fluorophenyl)-1,4-dihydropyridine-3,5,6-tricarboxylic acid triethyl ester.

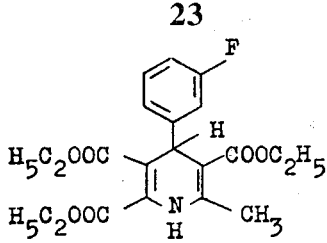

6.2 g of 3-fluorobenzaldehyde, 6.5 g of β-aminocrotonic acid ethyl ester and 9.5 g of oxalacetic acid diethyl ester in 40 ccs of ethanol are heated to the boil overnight, the mixture is evaporated in vacuo and a light yellow oil is obtained.

EXAMPLE 23

2-Methyl-4-(3'-fluorophenyl)-1,4-dihydropyridine-3,5-dicarboxylic acid diethyl ester-6-carboxylic acid.

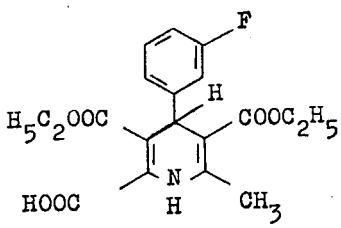

20 g of the triester obtained according to Example 22, in a solution of 1.15 g of sodium in 120 ccs of ethanol, are heated under reflux for 4–6 hours. Thereafter the monocarboxylic acid is precipitated with dilute sulphuric acid from the solution obtained after distilling off the alcohol and adding water. Yellow crystals of melting point 140° from ether, yield 55%.

EXAMPLE 24

2-Methyl-4-(4'-nitrophenyl)-1,4-dihydropyridine-3,5,6-triethyl ester.

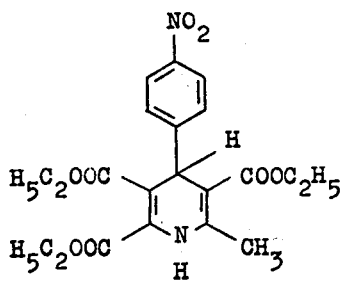

A solution of 30.2 g of 4-nitrobenzaldehyde, 38 g of oxalacetic acid diethyl ester and 26 g of β-aminocrotonic acid ethyl ester in 80 ccs of ethanol is heated to the boil overnight and subsequently evaporated in vacuo. Light yellow oil.

EXAMPLE 25

2-Methyl-4-(4'-nitrophenyl)-1,4-dihydropyridine-3,5-dicarboxylic acid diethyl ester-6-carboxylic acid.

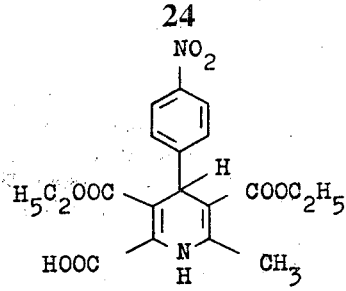

21.6 g of the triester (Example 24) in a solution of 1.15 g of sodium in 150 ccs of ethanol are heated for 6–8 hours to the boil, the mixture is concentrated in vacuo, the residue is taken up in water and the product is precipitated with dilute sulphuric acid. Yellow crystals of melting point 138° from ether, yield 45%.

EXAMPLE 26

2-Methyl-4-(3'-chlorophenyl)-1,4-dihydropyridine-3,5,6-tricarboxylic acid triethyl ester.

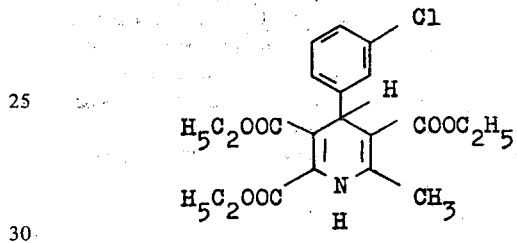

14 g of 3-chlorobenzaldehyde, 19 g of oxalacetic acid diethyl ester and 13 g of β-aminocrotonic acid ethyl ester in 60 ccs of ethanol are heated to the boil for several hours and subsequently evaporated in vacuo. Oil (orange). a. In the same way, 2-methyl-4-(2'-chlorophenyl)-1,4-dihydropyridine-3,5,6-tricarboxylic acid triethyl ester is prepared from 14 g of 2-chlorobenzaldehyde, 19 g of oxalacetic acid diethyl ester and 13 g of β-aminocrotonic acid ethyl ester in 60 ccs of ethanol.

EXAMPLE 27

2-Methyl-4-(3'-chlorophenyl)-1,4-dihydropyridine-3,5-dicarboxylic acid diethyl ester-6-carboxylic acid.

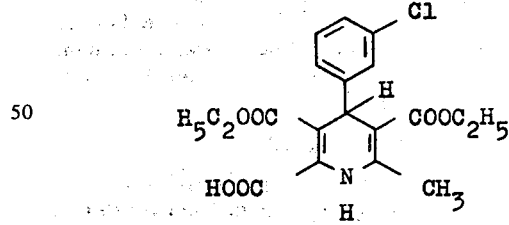

21.5 g of the triester manufactured according to Example 26, in a solution of 1.15 g of sodium in 150 ccs of ethanol, are heated to the boil for 4–6 hours. Thereafter the mixture is concentrated in vacuo, the residue is taken up in water and the product is precipitated with acid. Ochre-coloured crystals of melting point 137°, yield 35%. a. The 2-methyl-4-(2'-chlorophenyl)-1,4-dihydropyridine-3,5-dicarboxylic acid diethyl ester-6-carboxylic acid obtained in the same manner, as yellow crystals and in 55% yield, from the triester manufactured according to Example 26 a, has a melting point of

EXAMPLE 28

2-Methyl-4-(4'-methylmercaptophenyl)-1,4-dihydropyridine-3,5,6-tricarboxylic acid triethyl ester.

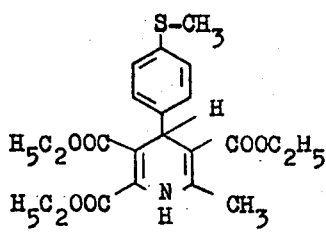

A solution of 7.6 g of 4-methylmercaptobenzaldehyde, 9.5 g of oxalacetic acid diethyl ester and 6.5 g of β-aminocrotonic acid ethyl ester in 40 ccs of ethanol is heated to the boil overnight and evaporated in vacuo. Oil (orange). a. In the same way, 2-methyl-4-(4'-methylmercaptophenyl)-1,4-dihydropyridine-3-carboxylic acid methyl ester-5,6-dicarboxylic acid diethyl ester is obtained from 7.6 g of 4-methylmercaptobenzaldehyde, 9.5 g of oxalacetic acid diethyl ester and 5.8 g of β-aminocrotonic acid methyl ester.

EXAMPLE 29

2-methyl-4-(4'-mercaptophenyl)-1,4-dihydropyridine-3,5-dicarboxylic acid diethyl ester-6-carboxylic acid.

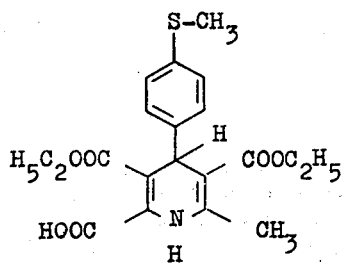

21.7 g of the triester manufactured in Example 28 are heated overnight in a solution of 1.15 g of sodium in 180 ccs of ethanol, the mixture is subsequently concentrated in vacuo, the residue is taken up in water and orange-yellow crystals of melting point 131° are precipitated with acid; yield 45%.

EXAMPLE 30

2-Methyl-4-(3'-methoxyphenyl)-1,4-dihydropyridine-3,5,6-tricarboxylic acid triethyl ester.

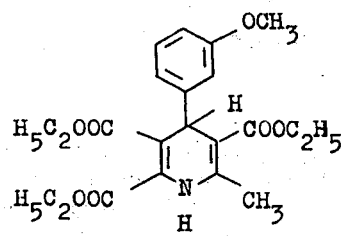

27.2 g of 3-methoxybenzaldehyde, 38 g of oxalacetic acid diethyl ester and 26 g of β-aminocrotonic acid ethyl ester in 120 ccs of ethanol are heated to the boil overnight and evaporated in vacuo. Oil (orange).

EXAMPLE 31

2-Methyl-4-(3'-methoxyphenyl)-1,4-dihydropyridine-3,5-dicarboxylic acid diethyl ester-6-carboxylic acid.

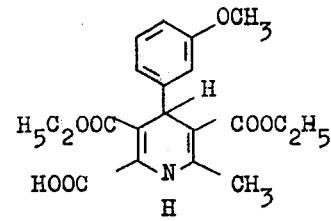

21 g of the triester manufactured according to Example 30, in a solution of 1.15 g of sodium in 200 ccs of ethanol, are heated to the boil for approx. 5 hours, the mixture is concentrated in vacuo, the residue is taken up in water and orange crystals of melting point 130° are precipitated with acid; yield 60%.

EXAMPLE 32

2-Methyl-4-(2'-α-biphenyl)-1,4-dihydropyridine-3,5,6-tricarboxylic acid triethyl ester.

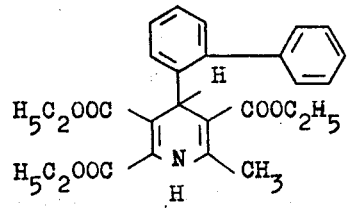

19.2 g of diphenyl-2-aldehyde (95% pure, boiling point 112°–115°/0.3), 19 g of oxalacetic acid diethyl ester and 13 g of β-aminocrotonic acid ethyl ester in 60 ccs of ethanol are heated to the boil overnight and evaporated in vacuo. Oil (orange-yellow).

EXAMPLE 33

2-Methyl-4-(2'-α-diphenyl)-1,4-dihydropyridine-3,5-dicarboxylic acid diethyl ester-6-carboxylic acid.

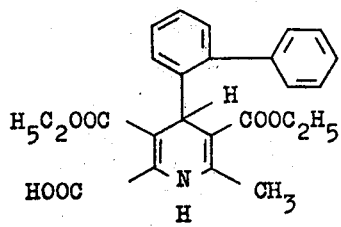

23 g of the triester manufactured according to Example 32, in a solution of 1.15 g of sodium in 180 ccs of alcohol, are heated to the boil for 6–8 hours, the mixture is concentrated, the residue is taken up in water and yellow crystals of melting point 111° are precipitated with acid; yield 40%.

EXAMPLE 34

2-Methyl-4-(2',4'-ditrifluoromethylphenyl)-1,4-dihydropyridine-3,5,6-tricarboxylic acid triethyl ester

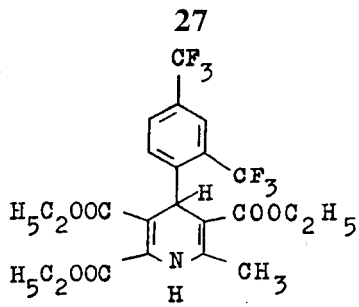

27 g of 2,4-di-(trifluoromethyl)-benzaldehyde, 19 g of oxalacetic acid diethyl ester and 13 g of β-aminocrotonic acid ethyl ester in 60 ccs of ethanol are heated to the boil overnight and subsequently evaporated in vacuo. Light yellow oil. a. In the same manner, 2-methyl-4-(2',5'-ditrifluoromethylphenyl)-1,4-dihydropyridine-3,5,6-tricarboxylic acid triethyl ester is obtained from 25.5 g of 2,5-di-(trifluoromethyl)-benzaldehyde, 19 g of oxalacetic acid diethyl ester and 13 g of β-aminocrotonic acid ethyl ester in 60 ccs of ethanol.

EXAMPLE 35

2-Methyl-4-(2',4'-ditrifluoromethylphenyl)-1,4-dihydropyridine-3,5-dicarboxylic acid diethyl ester-6-carboxylic acid.

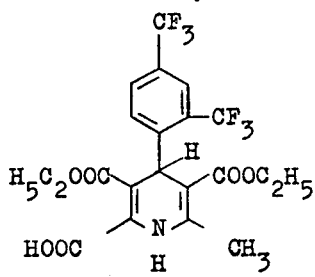

27 g of the triester manufactured according to Example 34, in a solution of 1.15 g of sodium in 150 ccs of ethanol, are heated for several hours to the boil, the mixture is evaporated, the residue is taken up in water and the product is precipitated with acid. Light yellow crystals of melting point 182° (ether), yield 60%. a. In the same manner, 2-methyl-4-(2',5'-ditrifluoromethylphenyl)-1,4-dihydropyridine-3,5-dicarboxylic acid diethyl ester-6-carboxylic acid, of melting point 70°–72°, is obtained in 35% yield from the triester obtained according to Example 34 a.

EXAMPLE 36

4-(3'-Methoxyphenyl)-1,4-dihydropyridine-2,3,5,6-tetracarboxylic acid tetraethyl ester.

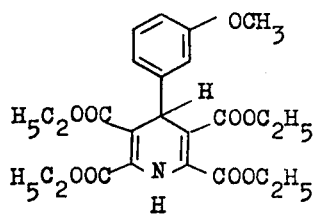

13.6 g of 3-methoxybenzaldehyde, 19 g of oxalacetic acid diethyl ester and 18.8 g of iminosuccinic acid diethyl ester in 50 ccs of ethanol are heated to the boil for several hours, and after evaporation a yellow oil is obtained.

EXAMPLE 37

4-(3'-Methoxyphenyl)-1,4-dihydropyridine-3,5-dicarboxylic acid diethyl ester-2,6-dicarboxylic acid.

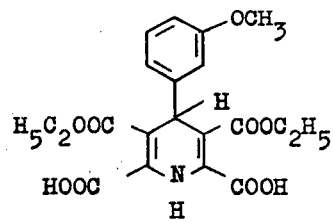

23.5 g of the tetracarboxylic acid ester manufactured according to Example 36, in a solution of 2.3 g of sodium in 250 ccs of ethanol, are heated to the boil overnight. The mixture is subsequently concentrated in vacuo, the residue is taken up in water and the product is precipitated with acid. Yellow crystals of melting point 160° (ether), yield 40%.

EXAMPLE 38

4-(3'-Chlorophenyl)-1,4-dihydropyridine-2,3,5,6-tetracarboxylic acid tetraethyl ester.

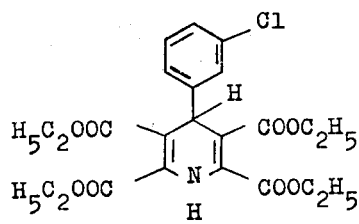

14.1 g of 3-chlorobenzaldehyde, 19 g of oxalacetic acid diethyl ester and 18.8 g of iminosuccinic acid diethyl ester in 60 ccs of ethanol are heated to the boil overnight and subsequently evaporated in vacuo. Yellow oil.

EXAMPLE 39

4-(3'-Chlorophenyl)-1,4-dihydropyridine-3,5-dicarboxylic acid diethyl ester-2,6-dicarboxylic acid.

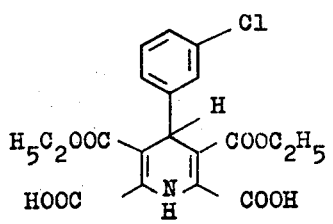

24 g of the tetraester obtained according to Example 38, in a solution of 2.3 g of sodium in 250 ccs of ethanol, are heated to the boil overnight, the mixture is concentrated in vacuo, the residue is taken up in water and yellow crystals of melting point 158° (ether) are precipitated with acid; yield 50%.

EXAMPLE 40

2-Methyl-4-(2'-azidophenyl)-1,4-dihydropyridine-3,5,6-tricarboxylic acid triethyl ester.

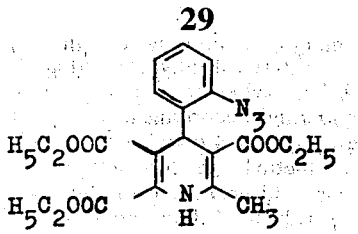

A solution of 14.7 g of 2-azidobenzaldehyde, 19 g of oxalacetic acid diethyl ester and 13 g of β-aminocrotonic acid ethyl ester in 40 ccs of ethanol is heated to the boil overnight and evaporated in vacuo. Yellow-brown oil.

EXAMPLE 41

2-Ethyl-4-(3'-nitrophenyl)-1,4-dihydropyridine-3,5,6-tricarboxylic acid triethyl ester.

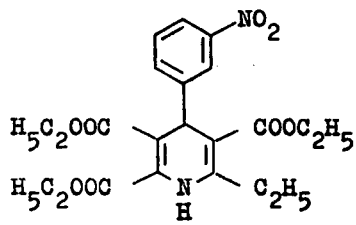

7.5 g of 3-nitrobenzaldehyde, 9.5 g of oxalacetic acid diethyl ester and 7.2 g of β-ethyl-β-aminoacrylic acid ethyl ester in 40 ccs of ethanol are heated to the boil for several hours, and after cooling, filtration and washing (ether/petroleum ether) yellow crystals of melting point 153°C are obtained in 68% yield.

EXAMPLE 42

2-Ethyl-4-(3'-nitrophenyl)-1,4-dihydropyridine-3,5-dicarboxylic acid ethyl ester-6-carboxylic acid.

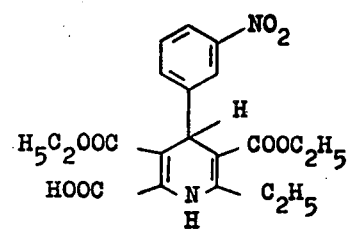

22.3 g of the triester produced according to Example 41 are added to a solution of 1.15 g of sodium in 100 ml of ethanol, the mixture is heated to the boil overnight and concentrated in vacuo, the residue is taken up in water and the product is precipitated with acid. Canary-yellow crystals (ether/petroleum ether) of melting point 140°C, yield 60%.

EXAMPLE 43

2-Methyl-4-(3'-nitrophenyl)-1,4-dihydropyridine-3-carboxylic acid methyl ester-5-carboxylic acid ethyl ester-6-carboxylic acid

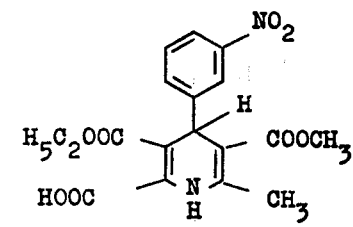

15 g of 3-nitrobenzaldehyde, 19 g of oxalacetic acid diethyl ester and 11.5 g of β-aminocrotonic acid methyl ester in 50 ccs of ethanol are heated to the boil under reflux for 8 hours and thereafter, following addition of a solution of 2.3 g of sodium in 100 ccs of ethanol, the whole is heated to the boil overnight and evaporated in vacuo, the residue is taken up in water and the product is precipitated with acid. Yellow-brown crystals of melting point 99°–100°C, yield 50%. a. In the same manner, 18.6 g of 3-nitro-6-chlorobenzaldehyde, 19 g of oxalacetic acid diethyl ester and 15 g of β-aminocrotonic acid ethyl ester in 80 ccs of ethanol give, after saponification, 2-methyl-4-(3'-nitrophenyl-6'-chlorophenyl)-1,4-dihydropyridine-3,5-dicarboxylic acid diethyl ester-6-carboxylic acid of melting point 176°–178°C, in yellow crystals and in 50% yield.

EXAMPLE 44

2-Methyl-4-(β-phenylethyl)-1,4-dihydropyridine-3,5,6-tricarboxylic acid triethyl ester.

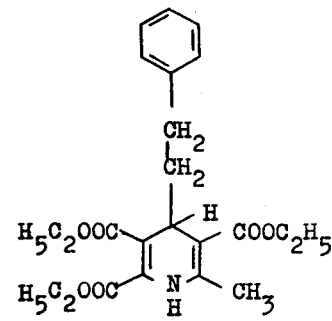

13.4 g of hydrocinnamaldehyde, 19 g of oxalacetic acid diethyl ester and 13 g of β-aminocrotonic acid ethyl ester in 40 ccs of ethanol are heated to the boil for several hours and subsequently evaporated in vacuo. Oil (yelloworange). a) In the same manner, 13.2 g of cinnamaldehyde, 19 g of oxalacetic acid diethyl ester and 13 g of β-aminocrotonic acid ethyl ester in 40 ccs of ethanol yield 2-methyl-4-styrryl1,4-dihydropyridine-3,5,6-tricarboxylic acid triethyl ester as an oil.

What is claimed is:

1. A compound of the formula:

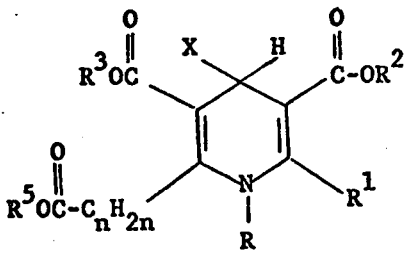

or a pharmaceutically acceptable non-toxic salt thereof, wherein

R is hydrogen, alkyl of up to 4 carbon atoms or alkenyl of up to 4 carbon atoms;

$R^1$ is hydrogen or alkyl of up to 4 carbon atoms; each of $R^2$ and $R^3$, taken independently of the other, is alkyl of up to 4 carbon atoms, hydroxy alkyl of up to 4 carbon atoms, alkoxy alkyl of up to 4 carbon atoms, alkenyl of up to 4 carbon atoms or alkynyl of up to 4 carbon atoms;

$R^5$ is hydrogen or alkyl of up to 4 carbon atoms; and

X is pyridyl unsubstituted or substituted by one or two members selected from the group consisting of alkyl of up to 4 carbon atoms, alkoxy of up to 4 carbon atoms, and halogeno; and n has a value of 0 to 3.

2. A compound according to claim 1 wherein $R^1$ is alkyl of up to 4 carbon atoms.

3. A compound according to claim 2 wherein R is hydrogen, $R^2$ and $R^3$ are alkyl of up to 4 carbon atoms and $R^5$ is hydrogen or alkyl of up to 4 carbon atoms.

4. The compound according to claim 1 which is 2-methyl-4-($\alpha$-pyridyl)-1,4-dihydropyridine-3,5-dicarboxylic acid dimethyl ester-6-acetic acid methyl ester.

5. The compound according to claim 1 which is 2-methyl-4-($\alpha$-pyridyl)-1,4-dihydropyridine-3,5,6-tricarboxylic acid 3-methyl ester-5,6-diethyl ester.

6. The compound according to claim 1 which is 2-methyl-4-($\beta$-pyridyl)-1,4-dihydropyridine-3,5,6-tricarboxylic acid triethyl ester.

7. The compound according to claim 1 which is 2-methyl-4-($\alpha$-pyridyl)-1,4-dihydropyridine-3,5,6-tricarboxylic acid triethyl ester.

8. The compound according to claim 1 which is 2-methyl-4-($\gamma$-pyridyl)-1,4-dihydropyridine-3,5,6-tricarboxylic acid triethyl ester.

* * * * *